(12) United States Patent
Mylonas

(10) Patent No.: US 10,744,023 B2
(45) Date of Patent: Aug. 18, 2020

(54) POSTURAL SUPPORT APPARATUS AND VENTILATION SYSTEM

(71) Applicant: Jim Mylonas, Markham (CA)

(72) Inventor: Jim Mylonas, Markham (CA)

( * ) Notice: Subject to any disclaimer, the term of this patent is extended or adjusted under 35 U.S.C. 154(b) by 485 days.

(21) Appl. No.: 15/210,286

(22) Filed: Jul. 14, 2016

(65) Prior Publication Data

US 2018/0014961 A1 Jan. 18, 2018

(51) Int. Cl.
*A61F 5/02* (2006.01)
*F41H 1/02* (2006.01)
*A41D 13/05* (2006.01)

(52) U.S. Cl.
CPC .......... *A61F 5/026* (2013.01); *A41D 13/0531* (2013.01); *F41H 1/02* (2013.01)

(58) Field of Classification Search
CPC ........ A41D 13/0531; A61F 5/026; F41H 1/02
See application file for complete search history.

(56) References Cited

U.S. PATENT DOCUMENTS 3,282,264 A * 11/1966 Connelly ................ A61F 5/026
450/96
2011/0184325 A1* 7/2011 Behzadian .............. A61F 5/026
602/19

\* cited by examiner

*Primary Examiner* — Anna K Kinsaul
(74) *Attorney, Agent, or Firm* — Elias Borges

(57) ABSTRACT

A postural support apparatus comprising is provided including an biasing body comprising: a top member; a bottom member, spaced from the top member; and a left and right resilient members attached at each end of the top and bottom members. The left and right resilient members are configured to bias the top and bottom members into a predetermined position. The support apparatus also includes a load distributor connected to the biasing body configured to distribute a load force applied to the postural support apparatus.

11 Claims, 8 Drawing Sheets

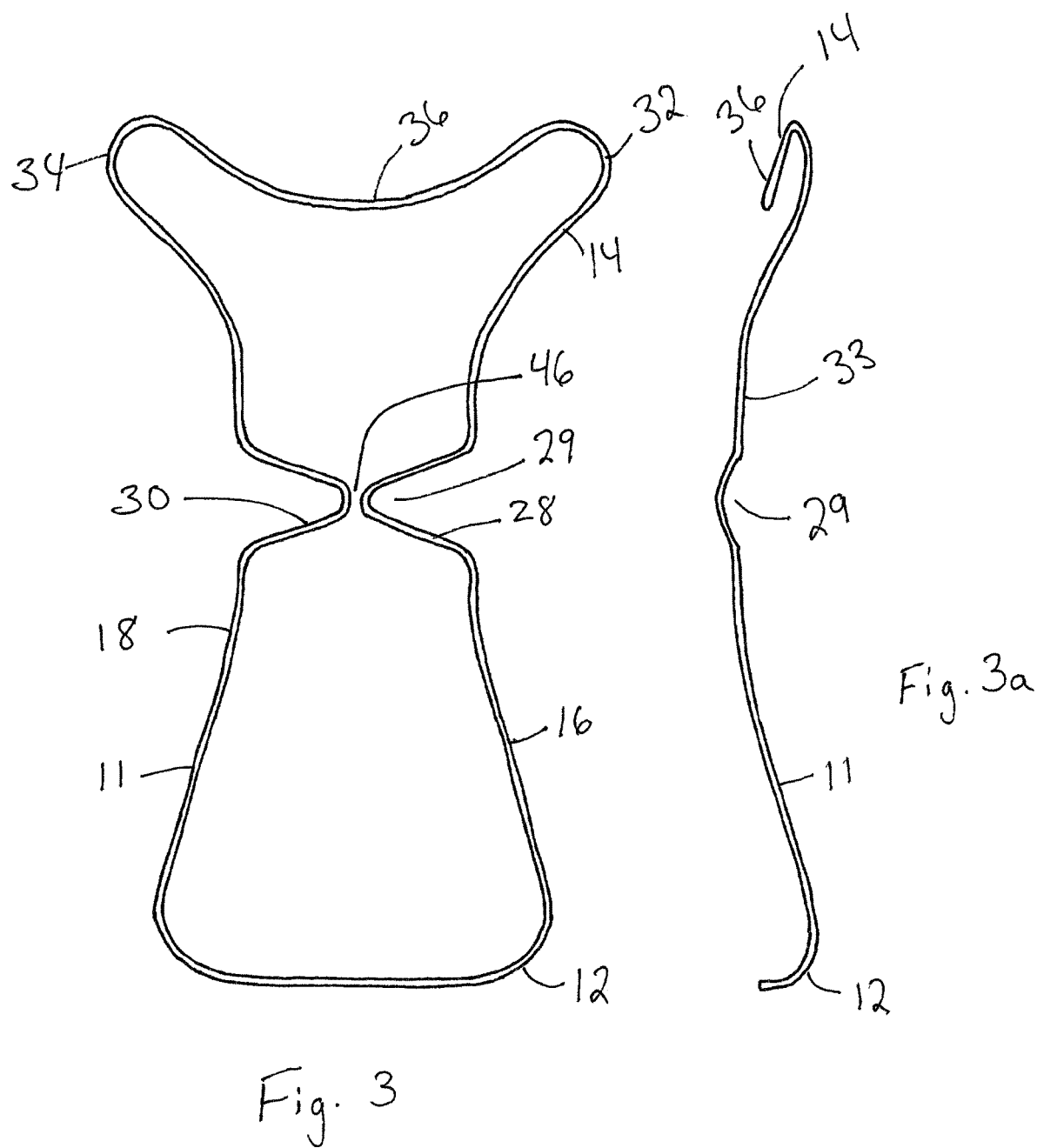

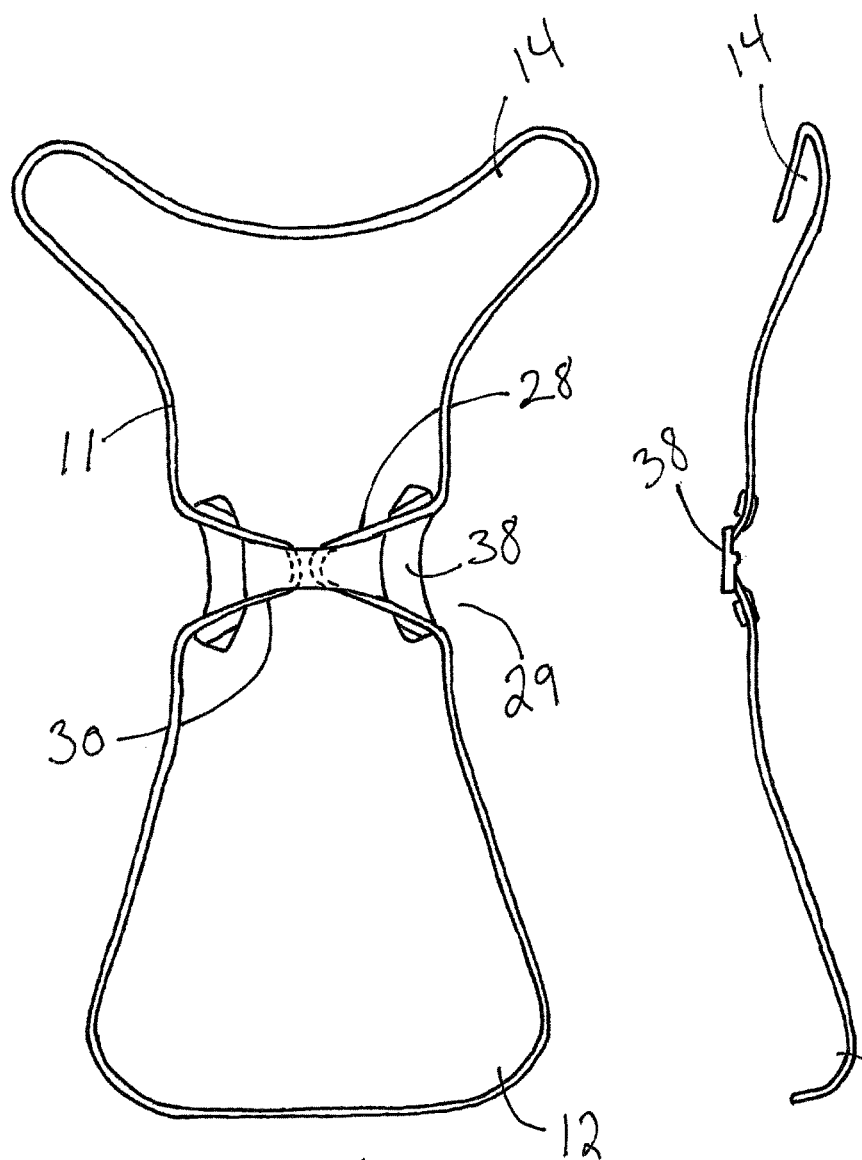

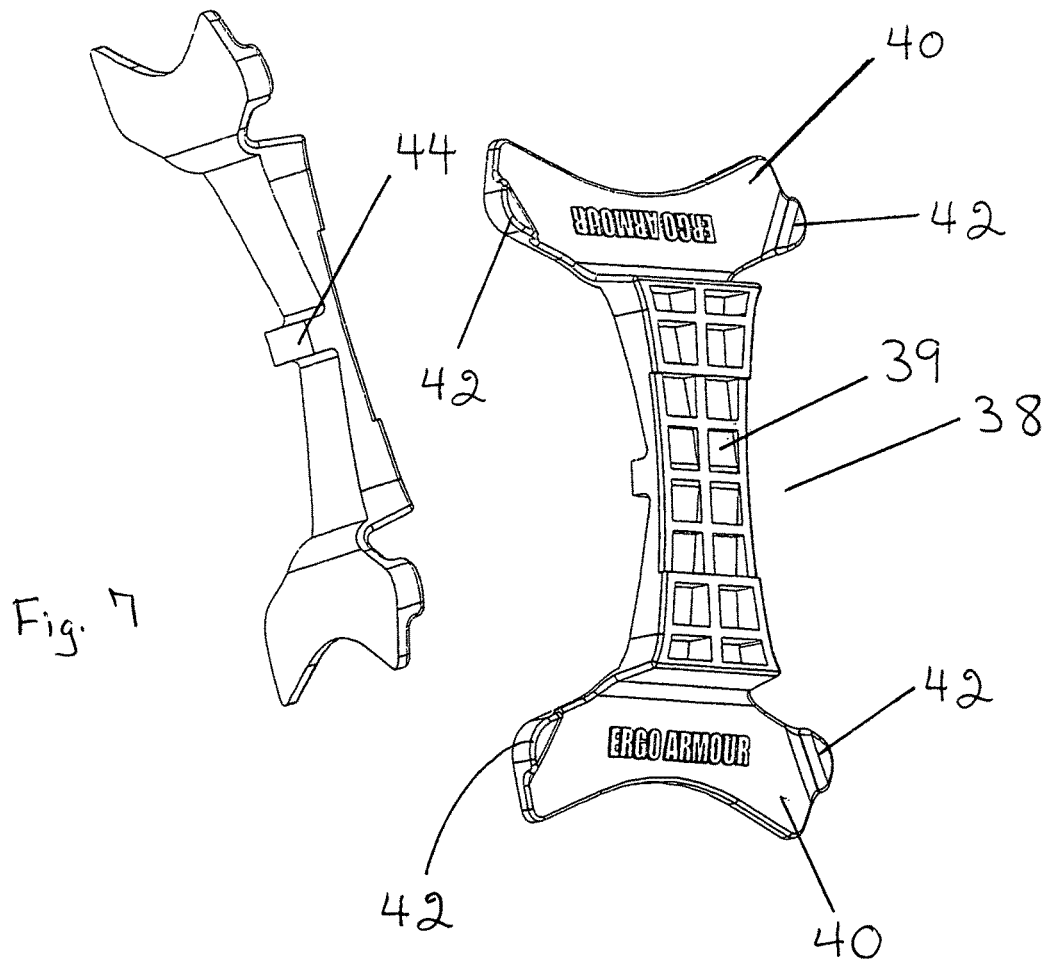

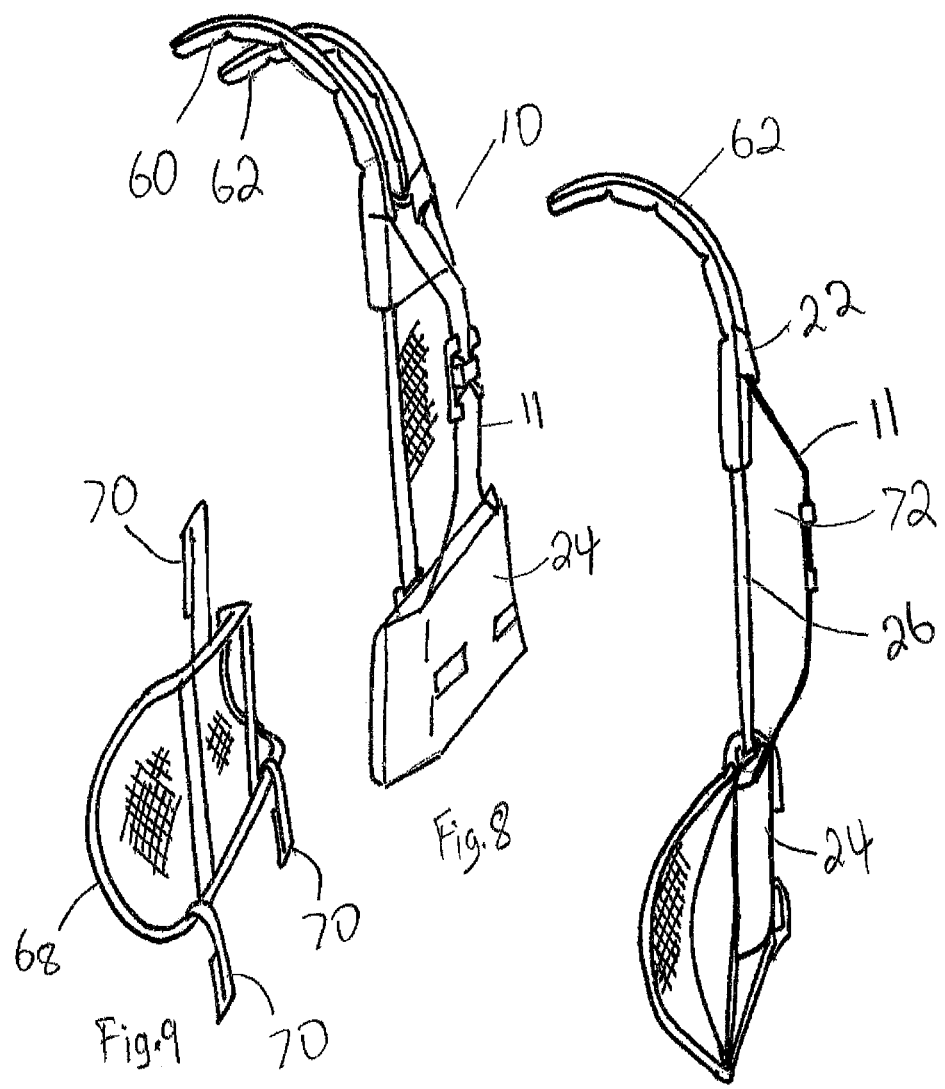

POSTURAL SUPPORT APPARATUS AND VENTILATION SYSTEM

BACKGROUND OF THE INVENTION

The present disclosure generally relates to portable equipment and in particular an apparatus for providing postural support and improved ventilation to a user while carrying portable equipment.

An ideal posture, also referred to as a neutral posture, may result from a proper alignment of the spine. The ideal posture may provide a wide variety of benefits, such as a lower amount of energy may be required to maintain any desired position and movement may facilitated within optimal bio-kinematic ranges. Achieving and maintaining the ideal posture may also reduce the stress placed on the body's tissues (for example, see Danis, C. G.; Krebs, D. E.; Gill-Body, K. M.; Sahrmann, S. (1998), *Relationship between standing posture and stability*, Journal of the American Physical Therapy Association, pp. 502-517). The ideal posture may also optimize breathing, oxygenation and circulation of bodily fluids such as lymph, cerebral spinal fluid, and blood.

Postural alterations or modifications that deviate from the ideal posture are known to be associated with numerous afflictions such as: general pain syndromes (for example, low back pain, neck pain, headaches); problems with specific joints (for example the hip and knee); problems with specific spinal regions (for example, loss of normal low back curve, cervical kyphosis and a reversal of normal neck curvatures); and various organ ailments (for example, uterine prolapse, gastric herniation, and impaired respiratory function). Postural alternations may also affect morbidity and mortality (for example, see Kado D M, Huang M H, Karlamangla A S, Barrett-Connor E, Greendale G A. Hyperkyphotic posture predicts mortality in older community-dwelling men and women: a prospective study. J Am Geriatr Soc 2004; 52:1662-1667; 28 Milne J S, Williamson J. A longitudinal study of kyphosis in older people. Age and Ageing 1983; 12:225-233 and Anderson F, Cowan N R. Survival of healthy older people. Br J Prev Soc Med 1976; 30:231-232).

The carrying of portable equipment may cause, or exacerbate, a person to deviate from the ideal posture. For example, soldiers and law enforcement personnel often wear personal body armor. Due to the rigid nature and necessary weight of the armor, to provide the desired protection, users of body armor often complain about lack of comfort and various ailments, which may be linked to deviating from the ideal posture.

SUMMARY OF THE INVENTION

A postural support apparatus is described further below. The apparatus comprises a biasing body which includes a top member, a bottom member spaced from the top member, and left and right resilient members attached at each end of the top and bottom members. The left and right resilient members are configured to bias the top and bottom members into a predetermined position. The support apparatus further includes a removable load distributor connected to the biasing body configured to distribute a load force applied to the postural support apparatus. A stabilizer is provided to link the left and right resilient members.

The apparatus may improve the comfort and posture of a user while carrying portable equipment. For example, the apparatus may be attachable to, or integrated with, various portable equipment including: personal body armor, backpacks, fire resistant equipment and clothing, respiratory systems, gas tanks and the like. Carrying such portable equipment may cause the user to deviate from an ideal posture. For example, personal body armor often includes storage pockets for ancillary equipment, such as ammunition and the like, on the front for ease of access. The rigidity of the armor, the overall weight of the armor and any ancillary equipment, an unequal weight distribution, and prolonged exposure are various factors that may contribute to a user deviating from the ideal posture.

The biasing member (resilient members) may bias the apparatus and the user towards a neural spine position while carrying portable equipment. Further, the load distributor may more evenly distribute the weight of the portable equipment through the user's lumbar region as well as lift weight off the user's shoulders.

BRIEF DESCRIPTION OF THE DRAWINGS

FIG. 3 is a dorsal view of the resilient unitary body portion of the postural support apparatus shown in FIG. 1;

FIG. 3*a* is a side view of the resilient unitary body portion of the postural support apparatus shown in FIG. 1;

FIG. 4 is a dorsal view of the biasing body portion of the postural support apparatus shown in FIG. 1.

FIG. 5 is a side view of the biasing body portion of the postural support apparatus shown in FIG. 1.

FIG. 6 is a dorsal isometric view of the stabilizer portion of the postural support apparatus made in accordance with the invention.

FIG. 7 is a ventral isometric view of the stabilizer portion of the postural support apparatus shown in FIG. 6.

FIG. 8 is an isometric view of the postural support apparatus shown in FIG. 1.

FIG. 9 is an isometric view of a lumbar support unit for use with the postural support apparatus shown in FIG. 8.

FIG. 10 is a side view of the postural support apparatus shown in FIG. 8 with the lumbar support unit shown in FIG. 9 attached thereto.

In the drawings like characters of reference indicate corresponding parts in the different figures.

DETAILED DESCRIPTION

Figure 1:
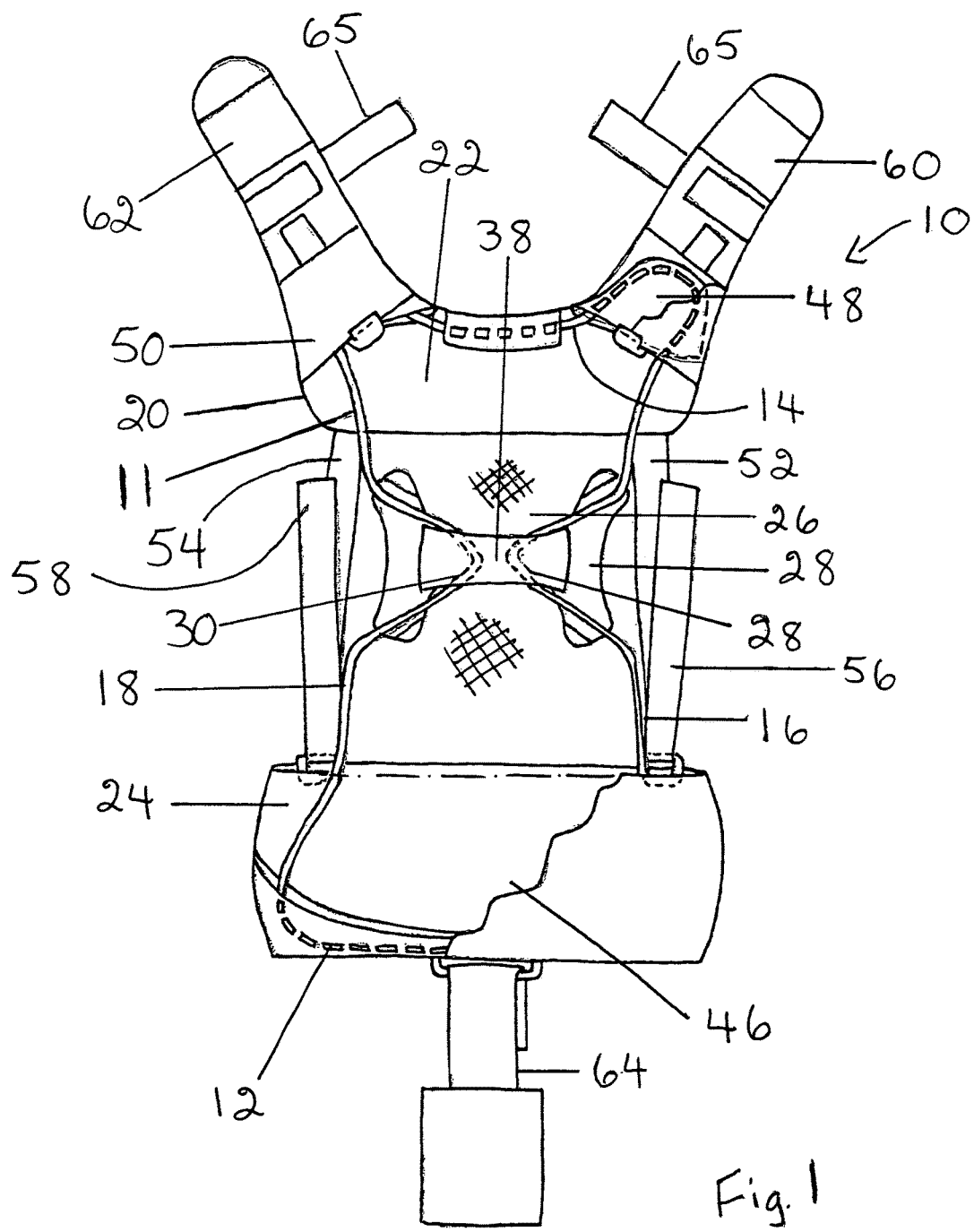
FIG. 1 is a dorsal view of an example postural support apparatus, in accordance with one embodiment of the present invention.

Referring firstly to FIG. 1, one embodiment of a postural support apparatus made in accordance with the present invention is shown generally as item 10 and includes a biasing body 11 mounted to a load distributor 20. The biasing body 11 has opposite top end 14 and bottom end 12 and opposite sides 16 and 18. Load distributor 20 has lower portion 24 and upper portion 22 which are configured to securely retain bottom ends 12 and top end 14, respectively. Vent member 26 is coupled to both portions 22 and 24 at opposite ends thereof. Load distributor 20 is made of a flexible and strong fabric and, preferably, vent member 26 is made of a fabric mesh which is capable of permitting air and moisture to pass there through. Sides 16 and 18 are flexible and resilient so as to bias portions 22 and 24 into a predetermined position (see FIG. 10) and keep vent member 26 taught.

Referring now to FIG. 3, biasing body 11 preferably comprises a single unitary spring like member. Body 11 could be formed as any spring like material such as fiberglass, plastic, carbon fiber, metal or composites thereof. Most preferably, body 11 consists of a loop of large gauge metal wire which is both resilient and flexible: essentially a large wire spring. Top end 14 of body 11 is formed as two lobes 32 and 34 with arched portion 36 between them which extends towards bottom end 12. Resilient sides 16 and 18 are bent towards each other at points 28 and 30, respectively, so that the space separating resilient sides 16 and 18 is narrowest at those points. This narrowing of the separation between the resilient sides permits body 11 to flex from side to side with greater ease. As best seen in FIG. 3*a*, body 11 is arched so that ends 14 and 12 are biased towards a predetermined position to form an arch with centre portion 29 positioned at the apex of the arch. As shall be discussed below, this arched shape permits the formation of an air space between the user's back and body 11. As can be seen in FIG. 4, a stabilizer 38 is positioned at center portion 29 to provide additional structural support. Portions 28 and 30 of biasing body 11 are secured around stabilizer 38 to secure the stabilizer and prevent center portions 28 and 30 from moving relative to each other which might cause collapse of the arch formed in biasing body 11.

Referring now to FIGS. 6 and 7, stabilizer 38 preferably consists of a plastic member having opposite ends 40, central body 39 and tabs 42 positioned at ends 40. One side of central body 39 has a raised portion 44 which is configured to fit in gap 46 of articulating body 11 (see FIG. 3). Ends 40 and tabs 42 are configured to permit the stabilizer to be threaded into the biasing body 11 such that the stabilizer is held securely by tension and raised portion 44 prevents the two sides of body 11 from physically touching.

Referring back to FIG. 1, bottom portion 24 of load distributor 20 has a pocket 46 which is dimensioned and configured to snugly retain end 12 of biasing body 11. Likewise, top portion 22 of load distributor 20 is provided with pockets 48 and 50 to snugly receive the lobes of end 14 of biasing body 11.

Figure 2:
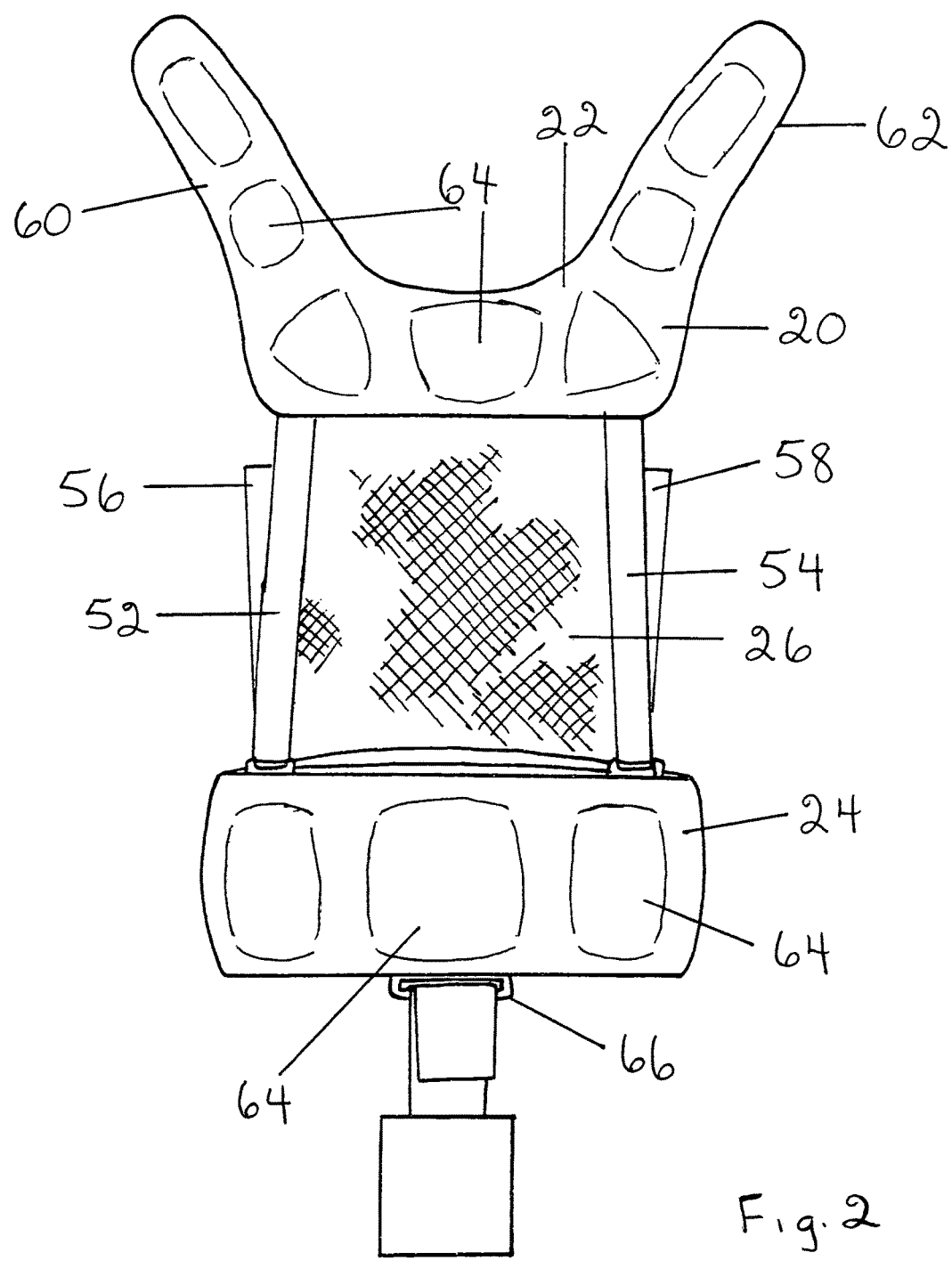
FIG. 2 is a ventral view of the postural support apparatus shown in FIG. 1.

Referring to FIGS. 1 and 2, adjustable straps 52 and 54 are provided between upper and lower portions 22 and 24 to permit a user to adjust the distance between the upper and lower portions of the load distributor by pulling on tabs 56 and 58. Ideally, the lengths of straps 52 and 54 are adjusted to keep vent member 26 taught.

Upper portion 20 is provided with shoulder extensions 60 and 62, which preferably consist of stiff but flexible extensions which help to distribute part of the weight born by the postural support apparatus off of the user's shoulders. Lower portion 24 is provided with an adjustable strap attachment 66 and upper portion 22 is provided with adjustable straps 65 for attaching to a body armor carrier or the like. Both portions 22 and 24 are provided with pads 64 to help make the postural support apparatus comfortable when worn.

Referring now to FIGS. 8, 9 and 10, a lumbar support member 68 can be provided which is releasably attachable to portion 24 by straps 70. As mentioned previously, air gap 72 is formed by the arch of biasing member 11 between the biasing member 11 and vent member 26.

Figure 11:
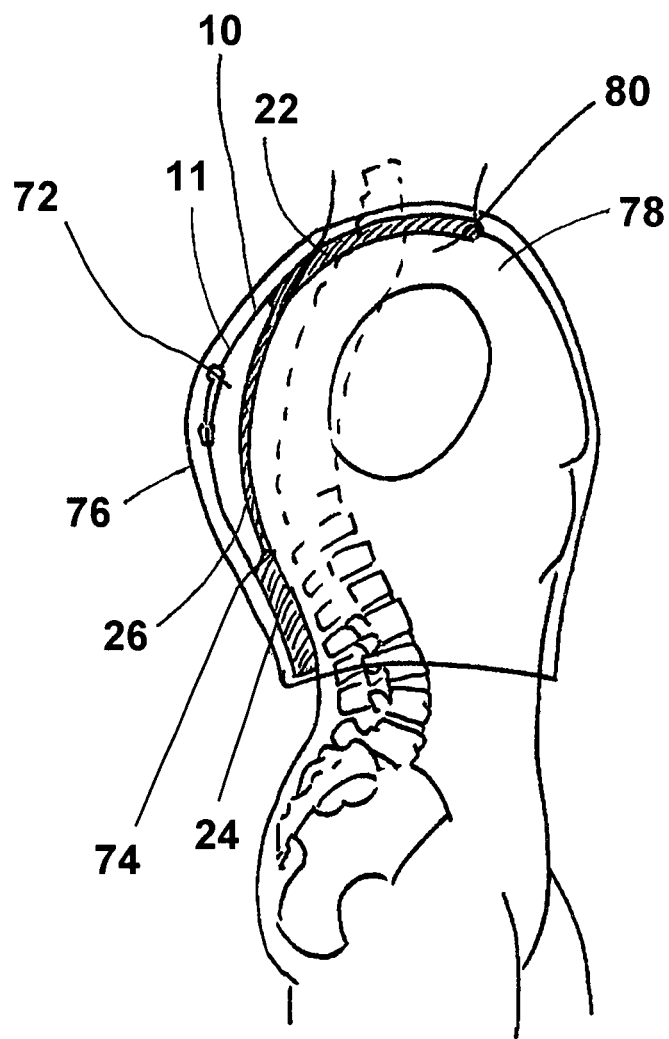
FIG. 11 is a sectional view of a person wearing the postural support apparatus of the present invention under body armor.
Figure 12:
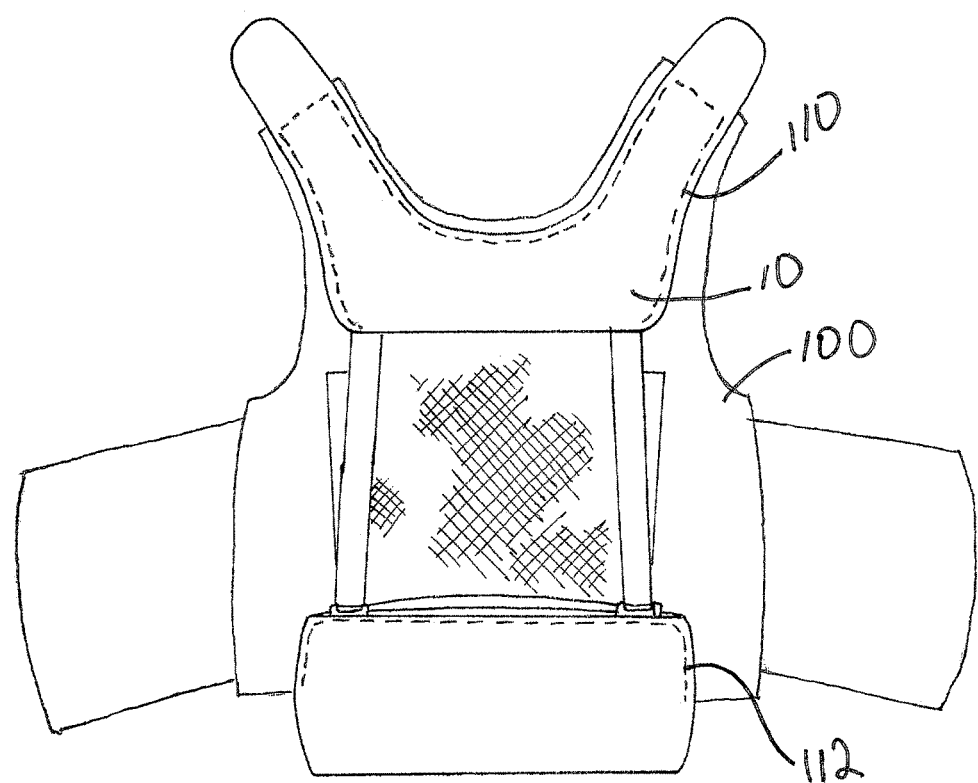
FIG. 12 is a ventral view of a body armor carrier (garment) having the postural support apparatus of the present invention incorporated therein.

Referring now to FIG. 11, user 78 can wear postural support apparatus 10 under body armor carrier 76. When so worn, the weight of the body armor and other equipment (not shown) carried on body armor carrier 76 is distributed more or less equally along the user's back 74 by means of upper portion 22, lower portion 24 and vent portion 26. Some of the weight is lifted off of the user's shoulders 80 by the extensions on the upper portion. Air gap 72 is maintained by biasing member 11 so that the user's back remains cool. Being flexible, postural support apparatus 10 can move and articulate while the user moves about. The resilient spring like nature of biasing member 11 ensures that the weight of the load is always distributed along the user's back and shoulders more evenly regardless of how the user moves. As shown in FIG. 12, a body armor carrier 100 can be constructed with postural support apparatus 10 pre-attached by means of stitching 110 and 112 or by other means known generally in the art such as adhesive bonding or zippers. This forms an integral structure which can be easier to use and which will have less play as the postural support apparatus will be more tightly held to the body armor carrier.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

What is claimed is:

1. A postural support apparatus comprising:
   a. a biasing body comprising:
      i. a top member having opposite right and left sides;
      ii. a bottom member, spaced from the top member, the bottom member having opposite right and left sides; and
      iii. a left and right resilient members attached at each of the right and left sides of the top and bottom members, respectively, wherein the left and right resilient members are configured to bias the top and bottom members into a predetermined position;
      iv. a stabilizer for linking the left and right resilient members at a point between the top and bottom members; and
   b. a load distributor connected to the biasing body configured to distribute a load force applied to the postural support apparatus;
   c) a vent member connected to the top member and the bottom member and spaced from a ventral surface of the biasing body, wherein the vent member is configured to provide a ventilation gap between a user and the biasing body,
   d. wherein the top and bottom members and the right and left resilient members form a resilient unitary body;
   e. wherein the resilient unitary body comprises a hoop made of a resilient material, the top member having right and left lobes.

2. The postural support apparatus of claim 1 wherein the top member has a middle portion positioned between the right and left lobes, the middle portion arching downwardly towards the bottom portion.

3. The postural support apparatus of claim 2 wherein the resilient unitary body comprises a hoop of wire made of resilient metal, each of the left and right resilient members comprising elongated left and right wire sections, respectively, a center portion of each of the left and right wire sections being curved towards each other such that a distance separating the left and right wire sections is greater towards top and bottom members and narrows at the centre portion, the stabilizer member linking the center portions of the left and right wire sections.

4. The postural support apparatus of claim 2 wherein the load distributor comprises a flexible web having opposite upper and lower portions and a vent member interposed between the upper and lower ends, the upper portion having left and right pockets configured to snugly retain the left and right lobes of the top member, respectively, the lower portion configured to securely retain the bottom member, the load distributor being further dimensioned and configured such that the vent member is positioned taught between the upper and lower portions by the biasing body and spaced from a ventral surface of the biasing body, wherein the vent member is configured to provide a ventilation gap between a user and the biasing body.

5. The postural support apparatus of claim 4 wherein the vent member comprises a fabric mesh.

6. The postural support apparatus of claim 4 wherein the load distributor further comprises a plurality of adjustable straps coupling the upper and lower portions, a distance separating the upper and lower portions being adjusted by adjusting the lengths of the adjustable straps.

7. A postural support apparatus comprising:
   a. a biasing body comprising:
      i. a top member;
      ii. a bottom member, spaced from the top member; and
      iii. an elongated resilient member having opposite left and right sides and opposite top and bottom ends, the top and bottom ends being attached to the top and bottom members, respectively, wherein the left and right sides of the elongated resilient member are configured to bias the top and bottom members into a predetermined position; and
   b. a load distributor connected to the biasing body configured to distribute a load force applied to the postural support apparatus, and
   c. wherein the elongated resilient member comprises an elongated heavy gauge wire loop, the left and right sides being left and right wire sections, respectively, the left and right wire sections being curved towards each other such that a distance separating the left and right wire sections is greater towards the top and bottom members and narrows at a middle portion between the top and bottom members.

8. The postural support apparatus of claim 7 further comprising a stabilizer member coupling the left and right wire sections at the middle portion.

9. The postural support apparatus of claim 8 further comprising a vent member extending between the top and bottom members and spaced from a ventral surface of the biasing body, wherein the vent member is configured to provide a ventilation gap between a user and the biasing body.

10. The postural support apparatus of claim 1 wherein the load distributor is built into a garment.

11. The postural support apparatus of claim 7 wherein the load distributor is built into a garment.

\* \* \* \* \*